United States Patent
Brothers

(10) Patent No.: US 7,482,504 B2
(45) Date of Patent: Jan. 27, 2009

(54) DRESSING FOR TREATMENT OF SHORT WOUNDS LOCATED IN HIGH TENSION AREAS

(75) Inventor: Lisa M. Brothers, Ingleside, IL (US)

(73) Assignee: Zymurgy, LLC, Ingleside, IL (US)

( * ) Notice: Subject to any disclaimer, the term of this patent is extended or adjusted under 35 U.S.C. 154(b) by 489 days.

(21) Appl. No.: 10/837,452

(22) Filed: Apr. 30, 2004

(65) Prior Publication Data

US 2005/0245855 A1 Nov. 3, 2005

(51) Int. Cl.
*A61F 13/00* (2006.01)

(52) U.S. Cl. .......................... 602/54; 606/213; 606/214; 424/78.25; 424/78.31; 424/78.32; 424/78.36

(58) Field of Classification Search .................... 602/52, 602/54–56, 213, 214, 42; 526/298, 297, 526/193, 194; 525/66, 77, 86, 88; 606/213–216; 424/443–445
See application file for complete search history.

(56) References Cited

U.S. PATENT DOCUMENTS

2005/0142172 A1* 6/2005 Kirsch et al. ................ 424/445

2006/0210528 A1* 9/2006 Askill et al. ............. 424/78.27

OTHER PUBLICATIONS

American Family Physician, Using Tissue Adhesive for Wound Repair: A Practical Guide to Dermabond, Bruns et al., Mar. 1, 2000.*
High Viscosity Dermabond Topical Skin Adhesive, Ethicon, Inc. 2003.*

* cited by examiner

*Primary Examiner*—Kim M Lewis
(74) *Attorney, Agent, or Firm*—Cherskov & Flaynik

(57) ABSTRACT

A dressing and method for treating high-tension wounds. First and second layers of a 1-butyl cyanoacrylate 16 adhesive are applied to a short, high-tension wound, with the first and second layers covering the wound and extending to at least about 2.5 mm (0.0984 in.) from each side of the wound. The first layer is allowed to set and polymerize before the second layer of 1-butyl cyanoacrylate is applied. The second layer extends at least about 2.5 mm (0.0984 in.) beyond each edge of the first layer. In the case of a long, high-tension wound, a third layer is applied after the first and second layers are allowed to set and polymerize. The third layer is at least about 2.5 mm (0.0984 in.) wide and is substantially perpendicular to the first and second layers. The third layer may occur intermittently every 2.5 cm (0.984 in.) over the length of the wound, and preferably extends at least about 5 mm (0.197 in.) beyond the edge of the first layer.

23 Claims, 1 Drawing Sheet

DRESSING FOR TREATMENT OF SHORT WOUNDS LOCATED IN HIGH TENSION AREAS

RELATED APPLICATIONS

The present application is related and claims priority of co-pending U.S. application Ser. No. 10/837,453, filed concurrently herewith and hereby incorporated by reference.

TECHNICAL FIELD

This invention relates generally to the treatment of a wound. More particularly, this invention relates to the treatment of a high-tension wound via the application of a 1-butyl cyanoacrylate material directly to the wound site.

BACKGROUND OF THE INVENTION

In the medical field, there are several different methods currently known for the treating and closing of wounds resulting from surgical incisions, lacerations, punctures and the like. Devices such as sutures, staples, skin tapes, and adhesives have been used when treating these different types of wounds. However, many of these devices have shortcomings. For example, sutures and surgical staples involve inflicting additional trauma to the wound surface since the needle or staple must pass through the tissue on the edges of the wound. Sutures and staples can also cause increased tension at the site, which will result in increased scarring. Further, when sutures and staples are used, the body treats them as foreign objects. This causes the body to increase its rate of reepithelialization at the wound site. The greater the rate of reepithelialization, the greater amount of scar tissue produced. Finally, sutures or surgical staples often require removal in a second procedure, resulting in additional inconveniences and potential discomfort to the patient.

Surgical strips, on the other hand, are typically used on superficial wounds due to their poor tensile strength. The low holding power of surgical strips causes the strips to prematurely fall off and the wound to open, particularly when in the presence of moisture. All of these examples hold true for wounds occurring in human and veterinary patients.

For these reasons, it has become more common for medical personnel to apply adhesives directly to a wound. For example, 1-butyl cyanoacrylate, commonly sold under the names Indermil™, Histacryl Blue™, and Vetbond™ have been used to aid in the closure of wounds. After the wound has reached homeostasis and the wound edges approximated, these materials are applied directly to the wound, permitting the wound to heal over time without the use of sutures, staples, and skin tapes. However, the use of 1-butyl cyanoacrylate has been thus far fairly limited. Due to the brittleness of the 1-butyl cyanoacrylate, the material has had problems flexing with the movement of the body. This led to the use of 1-butyl cyanoacrylate material in only short, low-tension wounds. When applied properly, 1-butyl cyanoacrylate has the potential for much more than what it is presently used for. Butyls are cheaper, easier, and faster to use than octyl cyanoacrylates.

Another type of material that is used in the medical field is 2-octyl cyanoacrylate, which is sold under the commercial name Dermabond™ and Nexaband™. 2-octyl cyanoacrylate is a type of glue that can be used on any area of the body for wounds of varying lengths and sizes. Currently, the recommended and approved technique for applying 2-octyl cyanoacrylate to a wound is by applying multiple layers of 2-octyl cyanoacrylate over the top of the wound. U.S. Pat. No. 6,479,725 to Brothers describes a technique for dressing high-tension wounds using octyl cyanoacrylate. However, this technique has problems; the tensile strength of the layers is higher than the surrounding skin. This causes dehiscence of the wound at either edge of the dressing, thus creating another wound or wounds needing repair. The patient experiences additional inconveniences and discomfort because the wound has to be treated again. If the dehiscence happens more than 24 hours after an injury, all of the patient's wounds will have to be sutured due to the increased risk of infection.

The present invention improves on current techniques by limiting the layers necessary, and thereby decreasing the tensile strength. By decreasing the tensile strength, a tensile strength is achieved that is closer to skin's own strength and avoiding dehiscence. The present invention discloses a new dressing having a much lower tensile strength that is very close to the actual strength of human skin and animal hide. By creating new techniques that utilize fewer layers, less adhesive material is used, resulting in cost savings. Instead of using one vial for every four inches, one vial may be used for 5 to 6 inches.

1-butyl cyanoacrylates have also been polymerized for the use of wound closure inside the body. The development of oxyalkene, alkylene carbonate, alkyl ester and alkyl cyanoacrylate, among others, have facilitated this. The same principles of application techniques are applicable to internal and external use in both humans and animal patients. This opens the doors for many different advances in medical care.

SUMMARY OF THE INVENTION

A dressing and method for treating a high-tension wound, comprising the application of a first and second layer of 1-butyl cyanoacrylate to a short, high-tension wound, and a first, second and third layer to a long, high-tension wound, with each layer covering the wound or a portion of the wound and extending to at least about 5 mm from each side of the wound. For the short, high-tension wound, the first layer is allowed to set and polymerize before applying the second layer of 1-butyl cyanoacrylate adhesive. For the long, high-tension wound, the first and second layers are allowed to set and polymerize before applying the third layer of 1-butyl cyanoacrylate adhesive. In the case of a long, high-tension wound, the third layer is applied substantially perpendicular to the first and second layers, and occurs intermittently over the length of the wound.

It is therefore an object of the invention to provide an improved method for applying an adhesive material to a wound. It is a further object of the invention to provide a method for treating a wound with 1-butyl cyanoacrylate material that reduces or minimizes the amount of scarring around the wound site. It is still another object of the invention to provide a method of applying 1-butyl cyanoacrylate material to a wound that reduces or minimizes dehiscence around the wound. It is yet another object of the present invention to provide a method for applying 1-butyl cyanoacrylate material to a high-tension wound that reduces or minimizes the occurrence of scarring and/or dehiscence around the wound site. Finally, it is another object of the present invention to provide a method of applying 1-butyl cyanoacrylate to a wound, such that an individual will have increased difficulty picking or peeling the material away from the wound.

These and other objects, advantages and features of the invention, together with organization and manner of operation thereof, will become apparent from the following detailed description when taken into conjunction with the

DETAILED DESCRIPTION

While the present invention is susceptible of embodiment in many different forms, this disclosure will describe in detail at least one preferred embodiment, and possible alternative embodiments, of the invention with the understanding that the present disclosure is to be considered merely as an exemplification of the principles of the invention and is not intended to limit the broad aspect of the invention to the specific embodiments illustrated.

Figure 1:
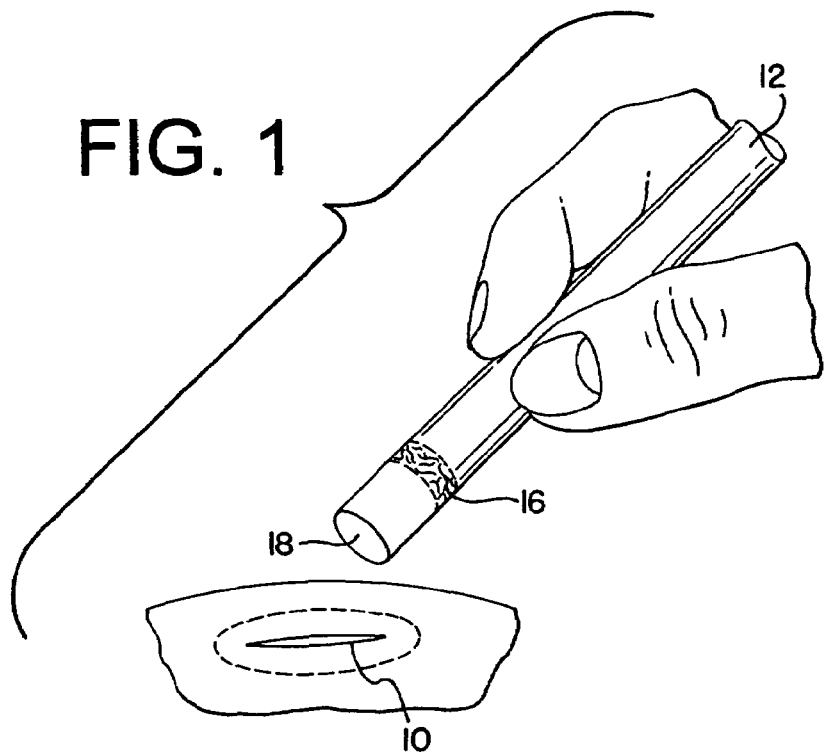
FIG. 1 is an isometric view of one embodiment of the present invention illustrating the application of cyanoacrylate to a wound site.
Figure 2:
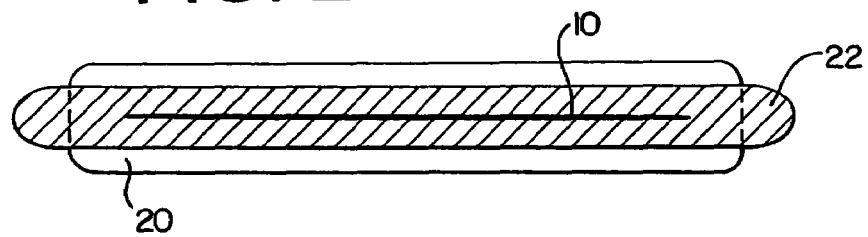
FIG. 2 is a top view of one embodiment of the present invention illustrating a wound after two layers of cyanoacrylate have been applied.
Figure 3:
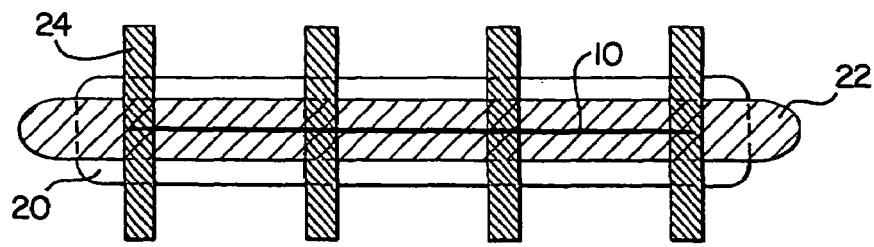
FIG. 3 is a top view of one embodiment of the present invention the wound after three layers of cyanoacrylate have been applied.

According to the present invention, with reference to FIGS. 1-3, the treatment of a wound comprises the use of the adhesive material 1-butyl cyanoacrylate 16. This topical skin adhesive is sold under the commercial name Indermil™, Histacryl Blue™, and Vetbond™ and is applied to a wound site 10 through the use of an applicator 12. A vial (not shown) inside the applicator 12 stores the unused 1-butyl cyanoacrylate 16 until application, and the material is applied to the wound site 10 via the applicator tip 18. While in the applicator 12, the unused 1-butyl cyanoacrylate 16 is in liquid form. The material will quickly set after it is applied to the wound site 10.

Under the present invention, 1-butyl cyanoacrylate 16 adhesive can be applied to wounds located both internally and externally on either a human or animal patient. More specifically, this invention is directed to high-tension wounds. The term "wound" is intended to include surgical incisions, lacerations, punctures and cuts, and the like. "High-tension" wound sites are defined as areas at or near a joint, and include areas at or near an elbow or knee. Other high tension areas are mid-sternal chest, post cesarean section wound, and joint replacement surgeries. It is important to provide extra tensile strength to high-tension wounds to prevent a high rate of reepithelialization that causes severe scars. In the case where the wound is located in a high tension area, the joint should preferably be tensioned to at least about a 45-degree angle before applying the adhesive in order to compensate for any stretching of the area that may occur after application.

In one embodiment of the present invention, 1-butyl cyanoacrylate 16 is applied to a wound site 10 as shown in FIGS. 1-3. After the wound site 10 is defined and cleaned, the user squeezes the applicator 12, causing some 1-butyl cyanoacrylate 16 to seep through the applicator tip 18. The user then applies multiple layers of 1-butyl cyanoacrylate 16 to the wound site 10 according to the present invention.

The present invention is directed to both short, high-tension wounds and long, high-tension wounds. A short, high-tension wound is a wound that is about 2.5 cm (0.984 in.) or smaller. A long, high-tension wound is a wound that is greater than about 2.5 cm (0.984 in.). When treating a short, high-tension wound preferably two separate layers, a first layer 20 and a second layer 22 of adhesive material are applied to wound site 10, with none of the layers 20 and 22 extending more than about five millimeters away from the nearest edge of the wound site 10. The second layer 22 is preferably applied to the wound site 10 at least about ten to fifteen seconds after the first layer 20 has been applied, allowing the first layer 20 to properly set and polymerize. For long, high-tension wounds where a third layer 24 is required, the third layer 24 is preferably applied about ten to fifteen seconds after the second layer 22 has been applied, allowing both the first layer 20 and the second layer 22 to properly set and polymerize. Before and while applying the layers 20, 22, and 24 the user may approximate the wound edges with their fingers while wearing latex-free gloves.

In one embodiment, for short, high-tension wounds, the first layer 20 should be applied directly over the wound site 10 extending at least about 5 mm (0.197 in.) from each edge of the wound site 10. After the first layer 20 has properly set and polymerized, the second layer 22 should be applied directly over the wound site 10 extending at least about 2.5 mm (0.0984 in.) beyond both sides of the wound site 10. The second layer 22 should cover a portion of the first layer 20, and the second layer 22 should also extend at least about 2.5 mm (0.0984 in.) beyond the first layer 20 on both ends as shown in FIG. 2. It is important that at least 2.5 mm (0.0984 in.) of the extending edge of the second layer 22 covers the first layer 20. Under this arrangement, the application allows the tension, created by the layers, to be more evenly distributed across the material covering the wound site 10. This placement also aids in more evenly distributing the tension created by 1-butyl cyanoacrylate while increasing the overall strength of the dressing.

Additionally, there are other variations to the method previously described for applying 1-butyl cyanoacrylate to a long, high-tension wound. For example, the first layer 20 should be applied directly over the wound site 10 extending at least about 5 mm (0.197 in.) from each edge of the wound site 10. After the first layer has properly set and polymerized, the second layer 22 should be applied directly over the wound site 10 extending at least about 2.5 mm (0.0984 in.) beyond both sides of the wound site 10. The second layer 22 should cover a portion of the first layer 20. The second layer 22 will also extend at least about 2.5 mm (0.0984 in.) beyond the first layer 20 on both ends. After the second layer 22 has properly set and polymerized, the third layer 24 should be applied so that it covers a portion of the first layer 20, a portion of the second layer 22, and a portion of the wound site 10. The third layer 24 may be a strip that is at least about 5 mm in width. The third layer 24 should be substantially perpendicular to the first and second layers 20 and 22, as well. Where the third layer is multiple strips, as shown in FIG. 3, the strips should occur at least about every 2.5 cm (0.984 in.) over the length of the wound site 10. The third layer 24 will extend beyond each edge of the first layer 20 by at least about 5 mm (0.197 in.). The additional third layer aids in strengthening the entire wound dressing and helps distribute the tension across the dressing. The enlarged surface area created by this application decreases the surface tension on the dressing. Furthermore, by decreasing the surface tension, the rate of reepithelialization is decreased.

In addition to the 1-butyl cyanoacrylate, the adhesive may comprise additional cyanoacrylate polymers including an oxyalkene, and alkylene carbonate, and alkyl ester and an alkyl cyanoacrylate. While preferred embodiments have been shown and described, it should be understood that changes and modifications can be made therein without departing from the invention in its broader aspects. For example, it is possible that 1-butyl cyanoacrylate could be applied in slightly different locations relative to the wound site, or that a different number of layers and orientations could be used to create an effective dressing. Furthermore, it is possible that other materials with properties similar to 1-butyl cyanoacrylate, such as a compound selected from the group consisting of oxyalkene, alkylene carbonate, alkyl ester, and alkyl 1-butyl cyanoacrylate, could be used on a wound while still creating an effective wound dressing in accordance with the invention's broader aspects. Various features of the invention are defined in the following claims:

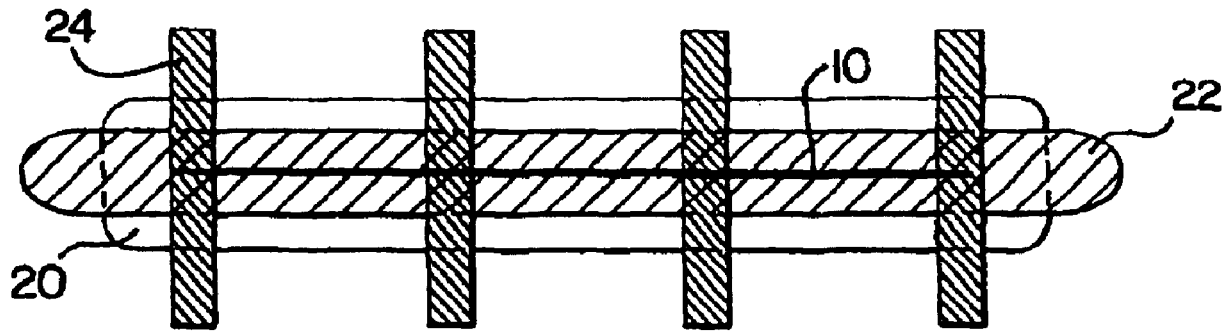

I claim:

1. A dressing for treating a short, high-tension wound consisting of: a first layer comprising a cyanoacrylate adhesive, the first layer is adapted to extend beyond each side of a short wound located in a high-tension area; wherein the first layer is polymerized over the wound; a second layer comprising a cyanoacrylate adhesive, the second layer is adapted to extend beyond each side of the wound.

2. The dressing of claim 1, wherein the first layer is adapted to extend to at least about 5 mm (0.197 inches) from each side of the wound.

3. The dressing of claim 2, wherein the second layer is adapted to cover at least about 2.5 mm (0.0984 inches) from each side of the wound.

4. The dressing of claim 3, wherein the second layer is adapted to extend at least about 2.5 mm (0.0984 inches) beyond each edge of the first layer.

5. The dressing of claim 4, wherein the short wound located in a high tension area is located on a joint, and the joint is at a 45 degree angle prior to application of the first layer of the adhesive.

6. The dressing of claim 1, wherein the second layer is adapted to cover at least about 2.5 mm (0.0984 inches) from each side of the wound.

7. The dressing of claim 6, wherein the second layer is adapted to extend at least about 2.5 mm (0.0984 inches) beyond each edge of the first layer.

8. The dressing of claim 1, wherein the cyanoacrylate adhesive comprises 1-butyl cyanoacrylate adhesive.

9. The dressing of claim 1, wherein the first layer further comprises a compound selected from the group consisting of oxyalkene, alkylene carbonate, alkyl ester, and alkyl cyanoacrylate.

10. The dressing of claim 1, wherein the second layer further comprises a compound selected from the group consisting of oxyalkene, alkylene carbonate, alkyl ester, and alkyl cyanoacrylate.

11. The dressing of claim 1, wherein the first and second layers are located on the exterior surface of either a human or animal.

12. The dressing of claim 1, wherein the first and second layers comprise polymerized 1-butyl cyanoacrylate adhesive and are located on the interior surface of either a human or animal.

13. The dressing of claim 1, wherein the first and second layers are no more than about 2.5 centimeters (0.984 inches) or smaller.

14. A dressing for treating a short, high-tension wound comprising: a first layer comprising 1-butyl cyanoacrylate adhesive, the first layer is adapted to extend beyond each side of a short wound located in a high tension area; wherein the first layer is polymerized over the wound; and a second layer comprising 1-butyl cyanoacrylate adhesive, the second layer is adapted to extend beyond each side of the wound.

15. The dressing of claim 14, wherein the first layer is adapted to extend to at least about 5 mm (0.197 inches) from each side of the wound.

16. The dressing of claim 15, wherein the second layer is adapted to cover at least about 2.5 mm (0.0984 inches) from each side of the wound.

17. The dressing of claim 14, wherein the second layer is adapted to cover at least about 2.5 mm (0.0984 inches) from each side of the wound.

18. The dressing of claim 16, wherein the second layer is adapted to extend at least about 2.5 mm (0.0984 inches) beyond the edge of the first layer.

19. The dressing of claim 18, wherein the short wound located in a high tension area is located on a joint, and the joint is at a 45 degree angle prior to application of the first layer of the adhesive.

20. The dressing of claim 17, wherein the second layer is adapted to extend at least about 2.5 mm (0.0984 inches) beyond the edge of the first layer.

21. The dressing of claim 14, wherein the first and second layers are located on the exterior surface of either a human or animal.

22. The dressing of claim 14, wherein the first and second layers comprise polymerized 1-butyl cyanoacrylate adhesive and are located on the interior surface of either a human or animal.

23. The dressing of claim 14, wherein the first and second layers are no more than about 2.5 cm (0.984 inches) or smaller.

* * * * *

UNITED STATES PATENT AND TRADEMARK OFFICE
CERTIFICATE OF CORRECTION

PATENT NO. : 7,482,504 B2
APPLICATION NO. : 10/837452
DATED : January 27, 2009
INVENTOR(S) : Brothers It is certified that error appears in the above-identified patent and that said Letters Patent is hereby corrected as shown below:

Column 6,
Please add, lines 47-48
24. The dressing of claim 1 wherein the high-tension wound is located on an appendage wherein the appendage remains fully mobile.

Please add, lines 49-51
25. The dressing of claim 14 wherein the high-tension wound is located on an appendage wherein the appendage remains fully mobile.

Signed and Sealed this

Ninth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,482,504 B2  Page 1 of 2
APPLICATION NO. : 10/837452
DATED : January 27, 2009
INVENTOR(S) : Brothers It is certified that error appears in the above-identified patent and that said Letters Patent is hereby corrected as shown below:

Delete the title page and substitute therefore the attached title page showing the corrected number of claims in patent.

Column 6,
Please add, lines 47-48
24. The dressing of claim 1 wherein the high-tension wound is located on an appendage wherein the appendage remains fully mobile.

Please add, lines 49-51
25. The dressing of claim 14 wherein the high-tension wound is located on an appendage wherein the appendage remains fully mobile.

This certificate supersedes the Certificate of Correction issued March 9, 2010.

Signed and Sealed this

Thirtieth Day of March, 2010

David J. Kappos
*Director of the United States Patent and Trademark Office*

United States Patent
Brothers

(10) Patent No.: US 7,482,504 B2
(45) Date of Patent: Jan. 27, 2009

(54) DRESSING FOR TREATMENT OF SHORT WOUNDS LOCATED IN HIGH TENSION AREAS

(75) Inventor: Lisa M. Brothers, Ingleside, IL (US)

(73) Assignee: Zymurgy, LLC, Ingleside, IL (US)

( * ) Notice: Subject to any disclaimer, the term of this patent is extended or adjusted under 35 U.S.C. 154(b) by 489 days.

(21) Appl. No.: 10/837,452

(22) Filed: Apr. 30, 2004

(65) Prior Publication Data

US 2005/0245855 A1 Nov. 3, 2005

(51) Int. Cl.
*A61F 13/00* (2006.01)
(52) U.S. Cl. .......... 602/54; 606/213; 606/214; 424/78.25; 424/78.31; 424/78.32; 424/78.36
(58) Field of Classification Search .......... 602/52, 602/54–56, 213, 214, 42; 526/298, 297, 526/193, 194; 525/66, 77, 86, 88; 606/213–216; 424/443–445
See application file for complete search history.

(56) References Cited

U.S. PATENT DOCUMENTS

2005/0142172 A1* 6/2005 Kirsch et al. .......... 424/445

2006/0210528 A1* 9/2006 Askill et al. .......... 424/78.27

OTHER PUBLICATIONS

American Family Physician, Using Tissue Adhesive for Wound Repair: A Practical Guide to Dermabond, Bruns et al., Mar. 1, 2000.*
High Viscosity Dermabond Topical Skin Adhesive, Ethicon, Inc. 2003.*

* cited by examiner

*Primary Examiner*—Kim M Lewis
(74) *Attorney, Agent, or Firm*—Cherskov & Flaynik

(57) ABSTRACT

A dressing and method for treating high-tension wounds. First and second layers of a 1-butyl cyanoacrylate 16 adhesive are applied to a short, high-tension wound, with the first and second layers covering the wound and extending to at least about 2.5 mm (0.0984 in.) from each side of the wound. The first layer is allowed to set and polymerize before the second layer of 1-butyl cyanoacrylate is applied. The second layer extends at least about 2.5 mm (0.0984 in.) beyond each edge of the first layer. In the case of a long, high-tension wound, a third layer is applied after the first and second layers are allowed to set and polymerize. The third layer is at least about 2.5 mm (0.0984 in.) wide and is substantially perpendicular to the first and second layers. The third layer may occur intermittently every 2.5 cm (0.984 in.) over the length of the wound, and preferably extends at least about 5 mm (0.197 in.) beyond the edge of the first layer.

25 Claims, 1 Drawing Sheet